United States Patent [19]

Mische et al.

[11] Patent Number: 5,279,546
[45] Date of Patent: Jan. 18, 1994

[54] THROMBOLYSIS CATHETER SYSTEM

[75] Inventors: Hans A. Mische, St. Cloud, Minn.; Liberato A. Iannone, Des Moines, Iowa

[73] Assignee: Lake Region Manufacturing Company, Inc., Chaska, Minn.

[21] Appl. No.: 927,934

[22] Filed: Aug. 7, 1992

Related U.S. Application Data

[63] Continuation of Ser. No. 544,582, Jun. 27, 1990, abandoned.

[51] Int. Cl.$^5$ .............................................. A61B 17/20
[52] U.S. Cl. ................................. 604/22; 128/24 AA; 606/194; 604/101
[58] Field of Search ............... 128/24 AA; 604/19–22, 604/96–101; 606/159, 191, 192, 194

[56] References Cited

U.S. PATENT DOCUMENTS

| | | | |
|---|---|---|---|
| 4,274,423 | 6/1981 | Mizuno et al. | 128/675 |
| 4,610,662 | 9/1986 | Weikl et al. | 604/101 |
| 4,636,195 | 1/1987 | Wolinsky | 604/101 |
| 4,692,139 | 9/1987 | Stiles | 604/19 |
| 4,808,153 | 2/1989 | Parisi | 606/159 |
| 4,867,742 | 9/1989 | Calderon | 604/101 |
| 4,870,953 | 10/1989 | Don Michael et al. | 606/159 |

Primary Examiner—C. Fred Rosenbaum
Assistant Examiner—Michael Rafa
Attorney, Agent, or Firm—Grady J. Frenchlick

[57] ABSTRACT

An apparatus and method for dissolving and removing material which tends to occlude a body passage way, such as an artery. The device employs a dual catheter system arranged in coaxial fashion. Each of the catheters has an inflatable balloon at its distal tip. Inflating the two balloons occludes the body passage way both proximal and distal to the treatment area, thus isolating it from fluid contact with the rest of the body. Because concentric catheters are used, the distance between the balloons and hence the size of the treatment area is adjustable. The thrombolytic agent is infused through orifices in the inner catheter in the region between the two balloons. A piezo electric device supplies ultrasonic agitation within the treatment area. A pressure device monitors the body passage way for unsafe conditions. Aspiration is accomplished through one or more lumens in the outer catheter. Ultrasonic agitation may be employed with the aspiration also to break up masses of material which may be too big to pass through the exit lumen cross section.

12 Claims, 9 Drawing Sheets

THROMBOLYSIS CATHETER SYSTEM

This is a continuation of copending application Ser. No. 07/544,582 filed on Jun. 27, 1990.

CROSS REFERENCE TO CO-PENDING APPLICATIONS

The present application is related to Ser. No. 919,044, filed Jul. 23, 1992, and entitled Catheter Lumen Occluder, assigned to the same assignee.

BACKGROUND OF THE INVENTION

1. Field of the Invention

The present invention relates generally to devices used to clear obstructions in body passage ways, and more particularly, relates to means and methods of treating such obstructions by the infusion of chemical thrombolytic agents.

2. Description of the Prior Art

The use of catheter systems to treat various medical conditions has been known for some time. In treating a particular area within a body passage way, it is often desirable to isolate the treatment area from the rest of the body through the use of one or more balloons which may be inflated proximal and/or distal to the treatment area. U.S. Pat. No. 2,936,760 issued to Gants, U.S. Pat. No. 4,022,216 issued to Stevens, and U.S. Pat. No. 4,705,502 issued to Patel describe catheters designed for use in the urinary tract.

Such catheter systems are also used in other applications. U.S. Pat. No. 4,696,668 issued to Wilcox, for example, describes a catheter system for treatment of nasobiliary occlusions. Similarly, U.S. Pat. No. 4,198,981 issued to Sinnreich is used in intrauterine applications. U.S. Pat. No. 4,453,545 issued to Inoue teaches an endotracheal tube.

One of the most common applications for catheter systems is the treatment of occlusions within the cardiovascular system. A catheter system for venous applications is seen in U.S. Pat. No. 4,795,427 issued to Helzel. U.S. Pat. No. 4,636,195 issued to Wollinsky, U.S. Pat. No. 4,705,507 issued to Boyles, and U.S. Pat. No. 4,573,966 issued to Welkl et al., all describe catheter systems designed to infuse a liquid for the treatment of an arterial occlusion. Each of these devices has one or more balloons to occlude the artery during the treatment process.

U.S. Pat. No. 4,655,746 issued to Daniels et al. proposes the use of two concentric catheters each having its own occlusion balloon to adjustably isolate a portion of the body passage way. The Daniels et al. design, however, requires the use of the interlumenal space as a fluid passageway, thereby complicating the construction and operation of the device. Use of the interlumenal space as a fluid passageway also may undesirably alter the handling characteristics depending upon the specific application and the degree to which the interlumenal space is pressurized.

A recognition of the need the improve to efficiency of the infused liquid is found in U.S. Pat. No. 4,423,725 issued to Baran et al. Unfortunately, the system of Baran et al. employs a middle balloon for forcing the liquid into the side walls of the artery. For arteries having insufficient resiliency, the high pressures in the isolated area tend to be equalized by expelling fluid and/or occluding material past the occluding balloons and out of the treatment area. In extreme cases, rupture of the arterial wall may be envisioned.

SUMMARY OF THE INVENTION

The present invention provides an apparatus and method for treating an occlusion in a body passage way, such as an artery, through the infusion of a fluid. Two balloons are used to isolate the treatment area from the remainder of the body. Because each of the balloons is located at the distal end of a different one of two concentric catheters and the inner catheter is slidable with respect to the outer catheter, adjustment of the interballoon distance and, therefore, the size of the isolated treatment zone is easily accomplished. However, because the interlumenal space is not used as a fluid passage way, the interballoon distance can be rapidly modified to increase or decrease the size of the isolated treatment zone.

A thrombolytic agent is infused into the isolated treatment area through orifices in the inner catheter. The thrombolytic agent may be streptokinase, TPA, or a similar chemical agent. As the lesion within the treatment area is exposed to the thrombolytic agent, some of the material is dissolved and removed by aspiration through lumens in the outer catheter.

Efficiency of the treatment is greatly enhanced by agitating the treatment area at ultrasonic frequencies. Ultrasonic energy is supplied by transducer(s) attached to the inner catheter within the isolated treatment area. Similarly, efficiency of aspiration is enhanced by ultrasonic agitation in the region of the aspiration ports of the outer catheter.

A pressure sensor within the isolated area is used to maintain the pressure within safe limits. Excess pressure tends to circumvent the balloon seals at the ends of treatment area. Too little pressure may cause collapse of the arterial wall under extreme conditions.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
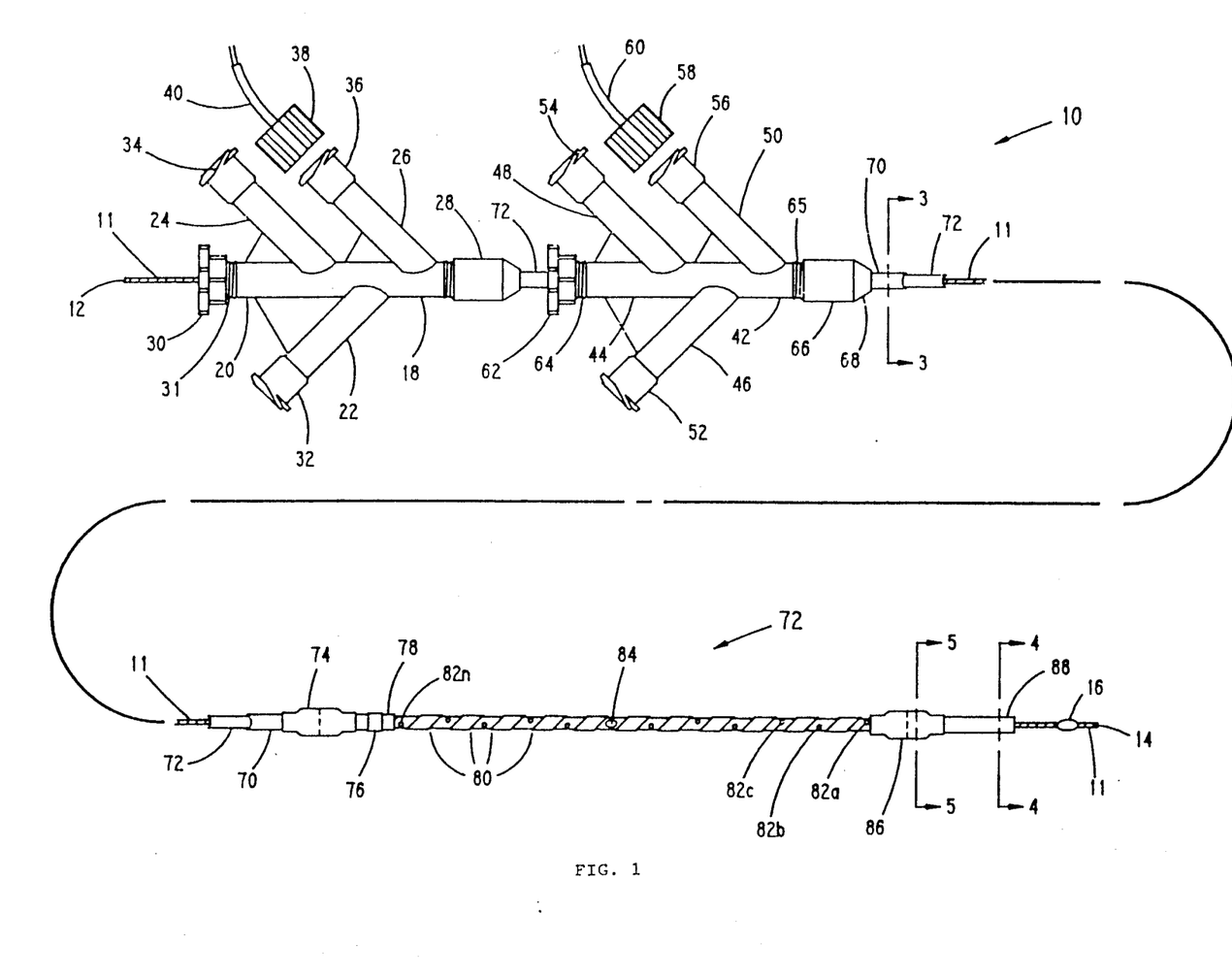
FIG. 1 is a plan view of a preferred embodiment of a catheter system employing the present invention.

FIG. 1 is a plan view of a thrombolysis catheter system 10 employing the present invention. The main body of catheter system 10 consists of a guide wire 11, an inner catheter 72, and an outer catheter 70, each of which is discussed in detail below.

At the proximal end of the catheter system, electrical and fluid access to the various lumens of catheter system 10 is provided by branch assemblies 18 and 42. Branch assembly 18 is at the most proximal end of catheter system 10. It consists of main branch 20 and secondary branches 22, 24, and 26. Main branch 20 couples to large open lumen 142 (shown in FIG. 3). This lumen is the pathway for guide wire 11, having proximal end 12 extending proximal to main branch 20 and having distal end 14 extending distal to the distal end of inner catheter 72. Guide wire 11 must be sealed to main branch 20 by screwing sealing nut 30 to threads 31.

Figure 3:
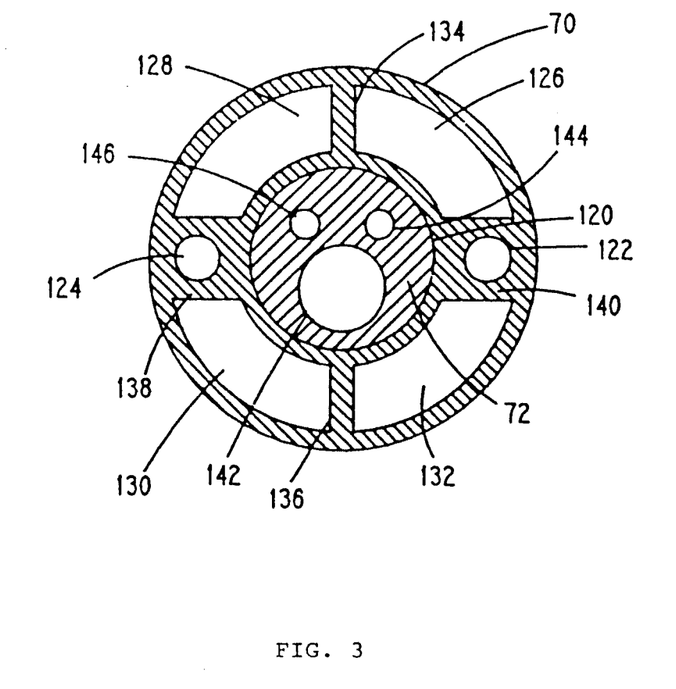
FIG. 3 is a cross-sectional view of the catheter system of FIG. 1.

Secondary branch 22 couples to inflation lumen 144 (see also FIG. 3). An inflation unit (not shown) is coupled to secondary branch 22 via standard hub 32. This permits inflation and deflation of balloon 86 at the distal end of inner catheter 72. Balloon 86 is used to provide the distal occlusion point of the isolated area under treatment.

Secondary branch 26 provides electrical coupling with electrical lumen 146 of inner catheter 72. This electrical coupling requires a minimum of two conductors to power the ultrasonic piezo-electric strip 80 (described below) which improves the efficiency of the system through agitation. Electrical plug 38 couples to standard hub 36 as further explained below. Cable 40 couples to an ultrasonic signal generator (not shown). An optional pressure transducer located on inner catheter 72 requires a third dedicated conductor and preferably shares one of the other two conductors which power the ultrasonic transducer.

Large open lumen 142 of inner catheter 72 is also used for infusion of the thrombolytic agent. To accomplish this, sealing nut 30 must firmly seal the proximal end of main branch 20 against guide wire 11 to prevent fluid from escaping proximally. Secondary branch 24 is also in fluid communication with large open lumen 142 of inner catheter 72. The thrombolytic fluid is introduced to the catheter system 10 via secondary branch 24 by coupling an appropriate pumping device (not shown) to standardized hub 34.

Branch assembly 18 is sealingly coupled to inner catheter 72 by threaded coupling 28. Inner catheter 72 is adjustably sealed to branch assembly 42 by sealing nut 62 tightly engaging threads 64. The adjustability provided by this configuration is required to provide adjustment of the interballoon spacing. Branch assembly 42, like branch assembly 18, is preferably molded of a rigid plastic. Electrical and fluid contact with the various lumens of outer catheter 70 is established by branch assembly 42.

Secondary branch 46 provides fluid coupling to balloon inflation lumen 122 (see also FIG. 3). A pumping device (not shown) is coupled to standard hub 52 of secondary branch 46 to permit inflation of balloon 74 of outer catheter 70. Inflation of balloon 74 occludes the artery proximal to the treatment area, which along with inflation of balloon 86 as discussed above, isolates the treatment area from the rest of the body.

Electrical lumen 124 (see also FIG. 3) of outer catheter 70 is coupled to secondary branch 50. In the preferred mode, two conductors are used in electrical lumen 124 to power ultrasonic transducer band 76. This element provides agitation adjacent to the aspiration ports to prevent clogging. Electrical plug 58 couples to standard hub 56 as further explained below. Cable 60 couples to an ultrasonic signal generator (not shown).

Fluid communication is established with aspiration lumens 126, 128, 130, and 132 by secondary branch 48. In operation a vacuum device (not shown) is coupled to standardized hub 54 of secondary branch 48. Aspiration removes the particles of occluding material as they are dissolved from the arterial wall by action of the thrombolytic agent.

Branch assembly 42 is sealingly coupled to outer catheter 70 at point 68 by tightly screwing threaded coupling 66 onto threads 65. The main length of catheter assembly 10 extends from sealing point 68 to balloon 74 and is about 150 cm.

Balloon 74 is inflated by standard means (e.g. pressurized sterile saline) from secondary branch 46 via inflation lumen 122. The major purpose of this balloon is to provide a proximal sealing of the treatment area. This sealing, combined with the distal seal of balloon 86, ensures that the body is not subjected to systemic side effects from the application of the thrombolytic agent. It also prevents particulate material released from the lesion from being circulated before it can be adequately aspirated.

Just distal of balloon 74 is ultrasonic transducer band 76. It is electrically coupled through electrical lumen 124 and secondary branch 50 to cable 60 and the ultrasonic signal generator. Ultrasonic transducer band 76 is preferably a commercially available piezoelectric strip. It is positioned adjacent the aspiration ports to provide agitation to improve aspiration efficiency. In the preferred embodiment shown, the aspiration ports are located at the very distal tip 78 of outer catheter 70.

Inner catheter 72 is slidingly engaged in lumen 120 of outer catheter 70 (see also FIG. 3). The sliding engagement permits the interballoon distance to be readily adjusted. As explained above, balloon 86 is inflated from secondary branch 22 through inflation lumen 122. The large open lumen 142 (see also FIG. 3) of inner catheter 72 is used as the lumen for guide wire 11. After the operational position has been achieved and both balloon 74 and balloon 86 have been inflated, large open lumen 142 is occluded at both proximal and distal ends to close it for use as an infusion lumen. Occlusion at the proximal end is accomplished by sealing nut 30 as explained above. Distal orifice 88 of large open lumen 142 may be occluded by positioning seal 16 sealingly against distal orifice 88. Alternative techniques for sealing orifice 88 are described below.

After the treatment area has been selected by sliding inner catheter within outer catheter 70, the treatment area has been isolated by inflation of balloons 74 and 86, and large open lumen 142 has been occluded both proximally and distally, the thrombolytic agent is infused through secondary branch 34. The thrombolytic agent is infused into the treatment area via orifices 82a, 82b, 82c, through 82n which are coupled to large open lumen 142. Efficiency of the system is improved by ultrasonic agitation supplied by commercially available piezo-electric strip 80, which is helically wound between the infusion orifices as shown. Piezo-electric strip 80 is electrically powered by conductors in electrical lumen 146 coupled through secondary branch 26 to cable 40.

A pressure transducer 84 is optionally positioned within the treatment zone to monitor pressure. This monitor permits coordination of infusion and aspiration volume to maintain the pressure within the isolated zone at a safe level.

Figure 2:
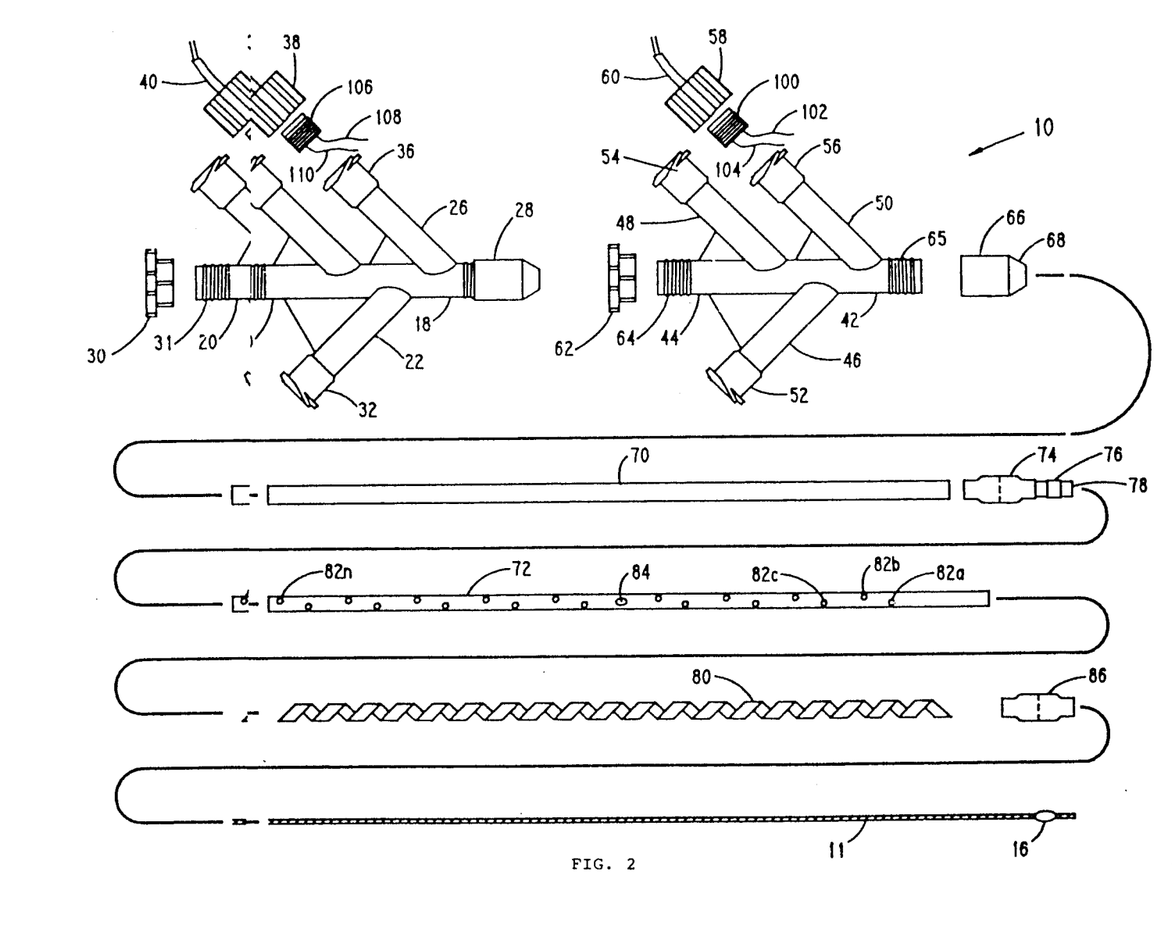
FIG. 2 is an exploded view of the catheter system of FIG. 1.

FIG. 2 shows an exploded view of the components of catheter system 10 wherein like reference numerals are as previously described. Of particular note are female electrical connectors 100 and 106 coupled to conductors 102 and 104, and conductors 108 and 110, respectively. Female electrical connectors 100 and 106 are fixedly attached within standard hubs 56 and 36, respectively. Additional detail is supplied below.

FIG. 3 is a cross sectional view of the main body of catheter system 10. It consists of inner catheter 72 snugly but slidably inserted into large central lumen 120 of outer catheter 70. Inner catheter 72 is extruded with large open lumen 142 which is used for the passage of guide wire 11 and for infusion of a thrombolytic agent as explained above.

Inner catheter 72 has two smaller lumens. Infusion lumen 144 is used to inflate balloon 86. Electrical lumen 146 carries the conductors which power piezo-electric strip 80.

Outer catheter 70 has a large central lumen 120 for passage of inner catheter 72. Infusion lumen 122 provides for inflation of balloon 74. Electrical lumen 124 provides for passage of the conductors to power ultrasonic band 76. Aspiration is performed through aspiration lumens 126, 128, 130, and 132. Each represents slightly less than 90 degrees of a coaxial, concentric lumen. Septal areas 134, 136, 138, and 140 separate aspiration lumens 126, 128, 130, and 132 and provide resistance to lumenal collapse.

Figure 4:
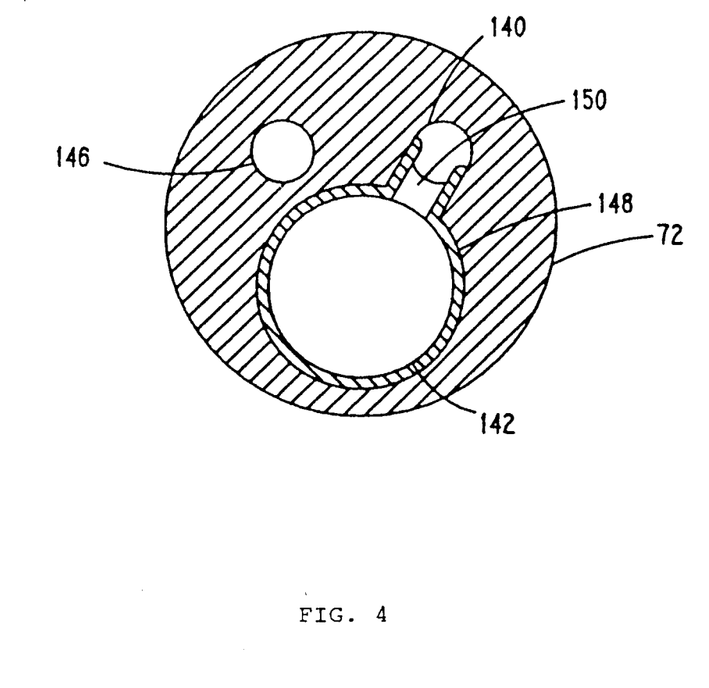
FIG. 4 is a cross-sectional view showing one method of occluding the open lumen of the inner catheter.

FIG. 4 is a cross sectional view of an alternative technique for occluding the distal end of large open lumen 142 prior to use for infusing the thrombolytic agent. In this embodiment, seal 16 may be omitted from guide wire 11 (see also FIG. 1). Occlusion of large open lumen 142 is accomplished by inflating interior balloon 148 from infusion lumen 144. Interior balloon 148 is expanded through interlumenal channel 150 to fill the cross sectional area of large open lumen 142 as shown. Additional details of the use of this technique are available in the commonly assigned, copending patent application entitled Lumen Occluder referenced above and incorporated herein by reference.

Figure 5:
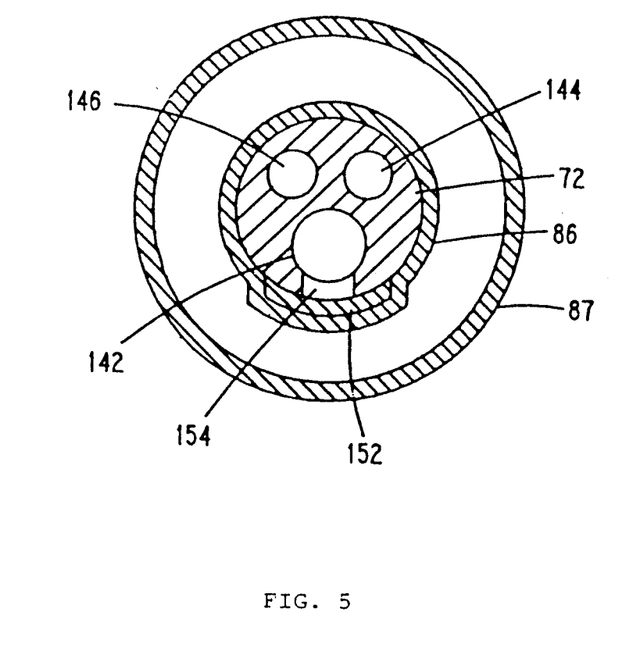
FIG. 5 is a cross-sectional view of an alternative means of occluding the open lumen of the inner catheter.

FIG. 5 is a cross sectional view of another alternative technique for sealing the distal end of large open lumen 142. With this approach, interior balloon 152 is located under balloon 86. When balloon 86 is inflated to position 87 by inflation port 144, interior balloon 152 is similarly inflated to fill interlumenal channel 154 and large open lumen 142. Again, further details concerning this technique may be found in the above referenced, commonly assigned, copending application.

Figure 6:
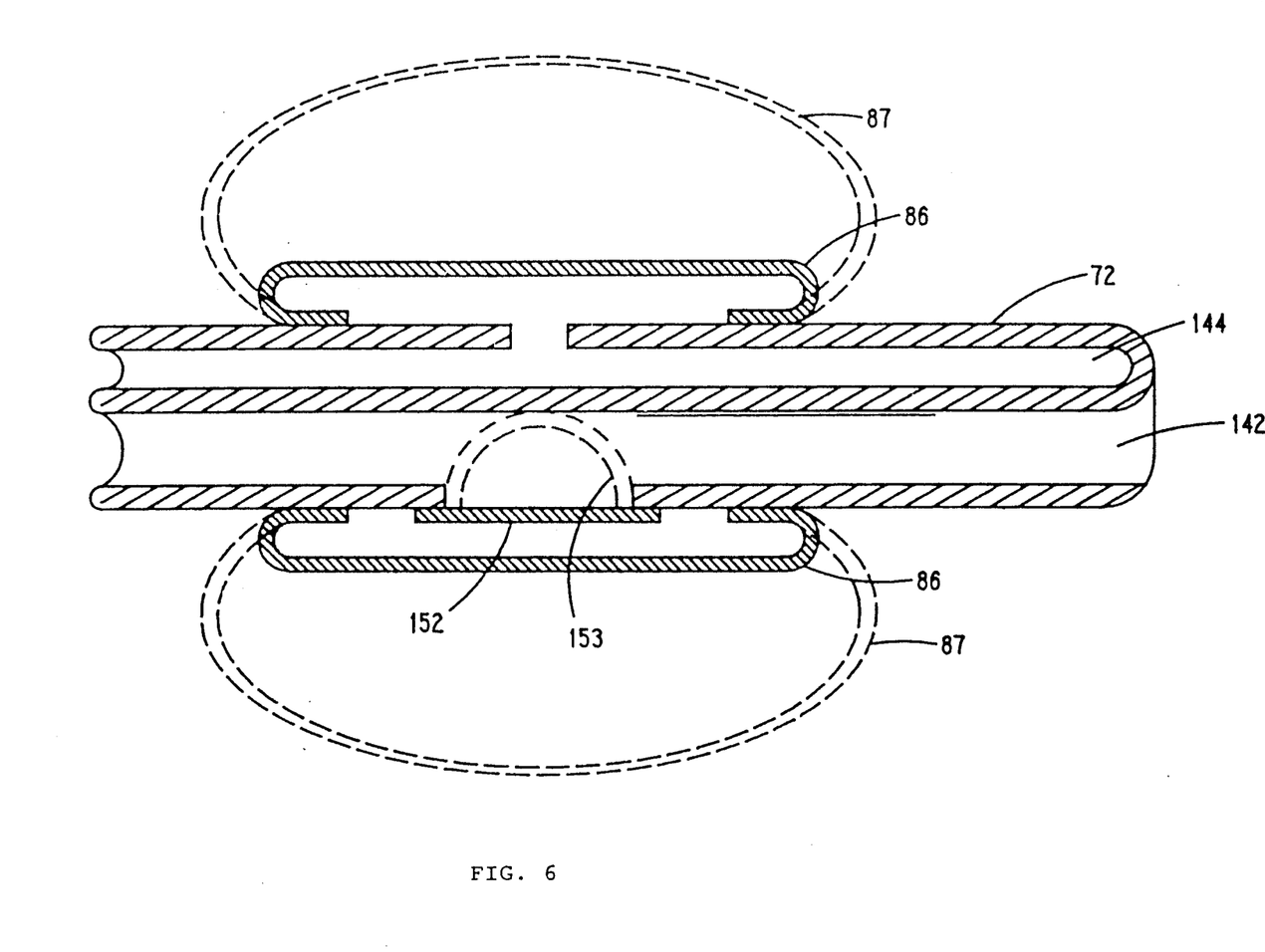
FIG. 6 is a longitudinal cross-sectional view of the embodiment of FIG. 5.

FIG. 6 is a longitudinally sectioned view of the alternative embodiment of FIG. 5, wherein referenced elements are as previously described. In this view, interior balloon 152 expands to position 153 when inflated.

Figure 7:
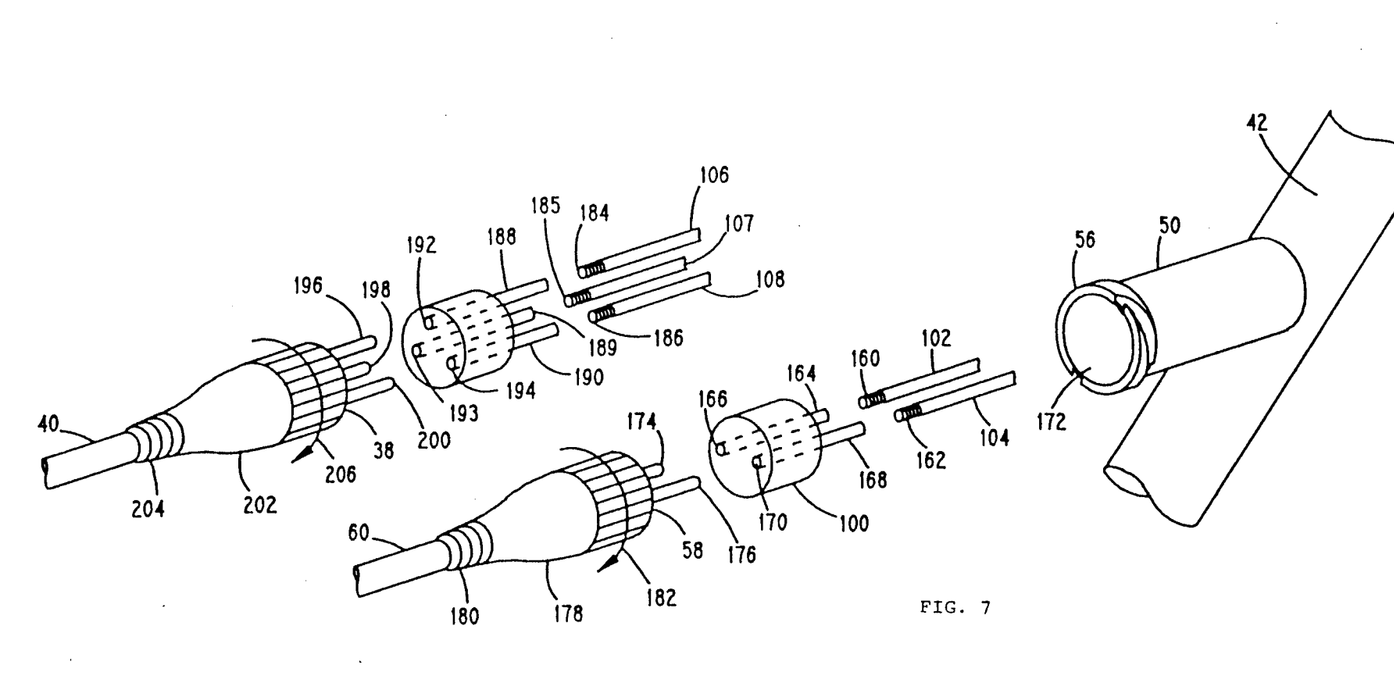
FIG. 7 is a detailed exploded view of the electrical connections at the proximal end of the catheter system.

FIG. 7 is an exploded view showing the detail of the electrical connections. Conductors run the length of electrical lumen 146 of inner catheter 72 from piezoelectric strip 80 (see also FIG. 1) to female connector 100. Distal tips 160 and 162 are electrically coupled to female sockets 164 and 168. Female connector 100 is frictionally engaged within grooved lumen 172 of hub 56.

Terminal pins 174 and 176 releasably engage within orifices 166 and 170, respectively, of female connector 100. Terminal pins 174 and 176 are electrically coupled to different ones of the conductors of cable 60. As explained above, cable 60 is coupled to an ultrasonic signal generator (not shown).

Terminal pins 174 and 176 are held in contact with female sockets 164 and 168, respectively, by rotation of electrical plug 58 in the direction of arrow 182 to engage with hub 56 as with conventional Luer assemblies. To facilitate the connection, electrical plug is provided with a smoothly sloping conical portion 178 and strain relief 180.

The electrical connection between electrical plug 38 and female socket 106 operates in similar fashion except that it contains an optional third conductor to accommodate pressure transducer 84 as explained above. Conductors 106, 107, and 108; distal tips 184, 185, and 186; female sockets 188, 189, and 190; orifices 192, 193, and 194; terminal pins 196, 198, and 200; smooth conical shape 202; and strain relief 204 functions as explained above.

Figure 8:
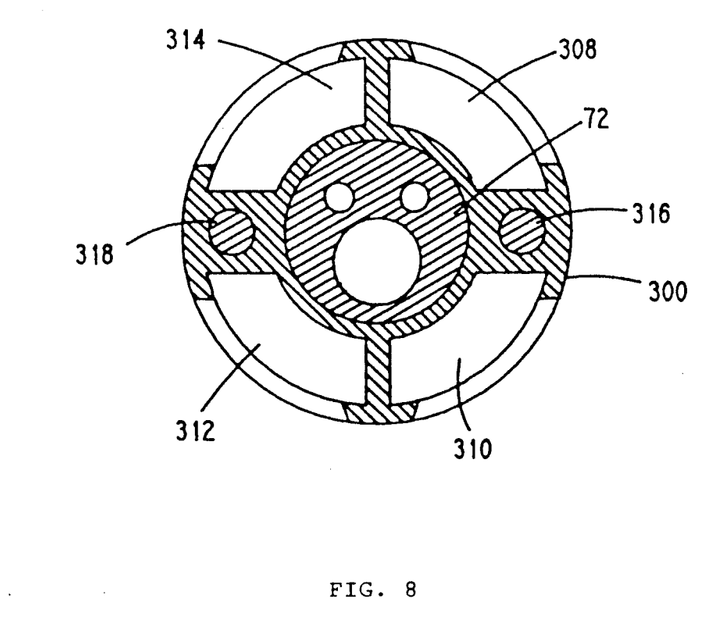
FIG. 8 is a cross sectional view of the aspiration ports of an alternative embodiment.

FIG. 8 is a cross sectional view of an alternative technique for implementing the aspiration ports. In the preferred mode of FIG. 1, outer catheter 70 is simply terminated at distal point 78 and therefore the aspiration lumens 126, 128, 130, and 132 are open in the distal direction. This configuration is most useful for very small diameter arteries.

In the alternative embodiment of FIG. 8, the aspiration ports are configured to open laterally, which works well with arteries of larger diameter. Aspiration ports 308, 310, 312, and 314 are in fluid communication with corresponding aspiration lumens as shown. The inflation and electrical lumens are sealed with plugs 316 and 318, respectively.

Figure 9:
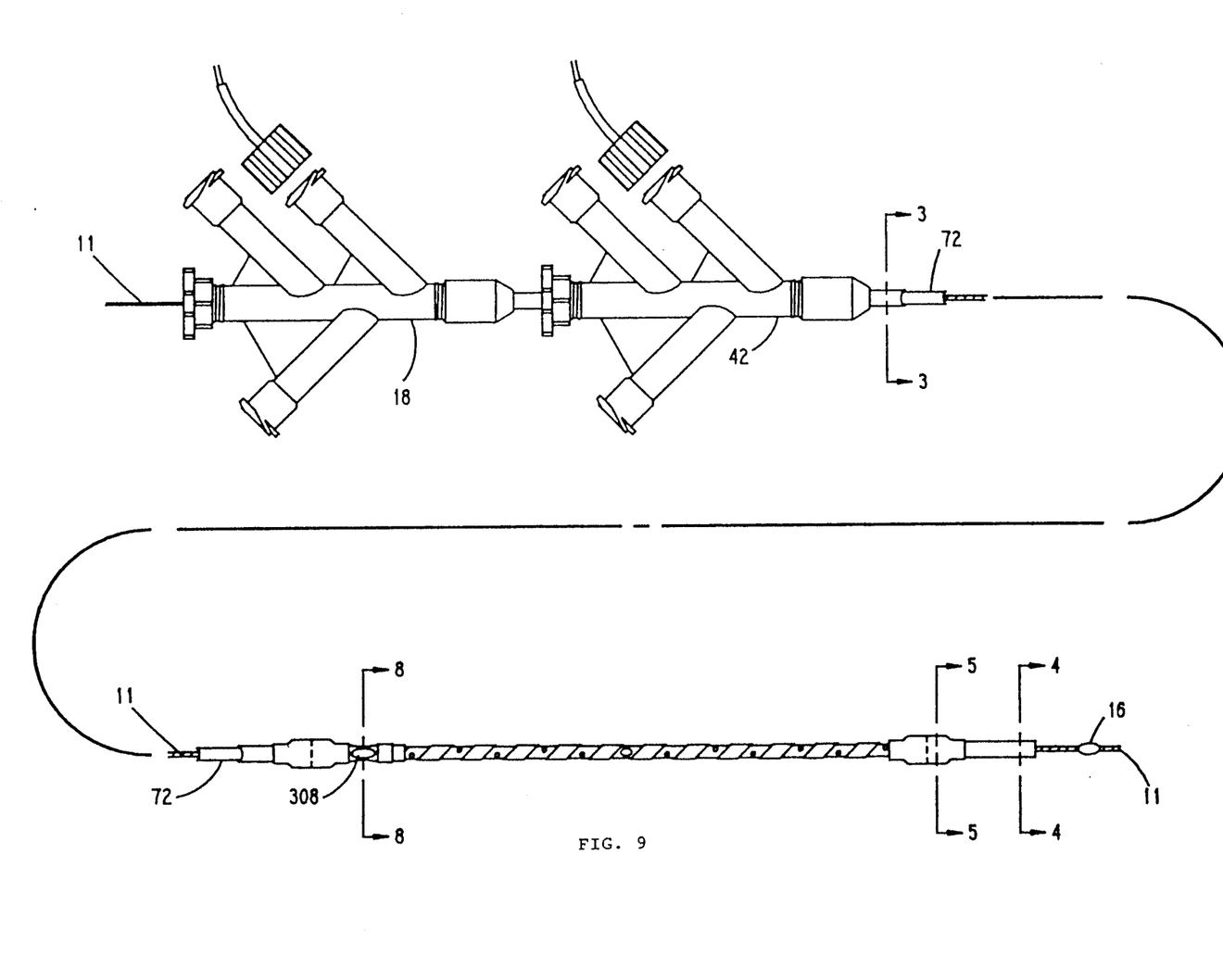
FIG. 9 is a plan view of the catheter system having the alternative embodiment of the aspiration ports.

FIG. 9 is a plan view of a thrombolytic catheter system which is identical to the catheter system of FIG. 1 except that it employs the aspiration ports shown in FIG. 8 of which only port 308 is shown.

Having thus described the preferred embodiments of the present invention, those of skill in the art will readily appreciate that other embodiments may be practiced without deviating from the scope of the claims hereto attached.

We claim:

1. A two catheter thrombolysis catheter system for the occlusion and treatment of a vessel obstruction comprising:

a. A first catheter having a catheter wall, a proximal end, a distal end, and first means for occluding a vessel located adjacent said first catheter distal end;

b. a second catheter having a catheter wall, a proximal end, a distal end, a central lumen which passes entirely through said second catheter and a second means for occluding a vessel located adjacent said second catheter distal end, said second catheter being slidingly engaged and coaxial with said first catheter so that the distance between said first means for occluding a vessel and said second means for occluding a vessel is variable and defines a treatment zone;

c. means in said second catheter for administering a thrombolytic agent into said treatment zone, said administering means including said central lumen of said second catheter and a plurality of radially disposed ports located in said second catheter wall between said first and second means for occluding a vessel, the ports being in fluid communication with said central lumen;

d. means in said central lumen of said second catheter for restricting the flow of thrombolytic agent therethrough;

e. means in said first catheter for aspirating said vessel, said aspirating means also being located between said first and second means for occluding a vessel; and f. means attached to said second catheter wall between said first and second means for occluding a vessel for supplying agitation energy in said vessel to said treatment zone.

2. A system according to claim 1 which further includes means associated with said second catheter wall for monitoring pressure within an occluded zone of a vessel.

3. A system according to claim 1 wherein said means for supplying agitation energy comprises a transducer.

4. A system according to claim 1 wherein the central lumen of said second catheter has a diameter which is slightly larger than that of a guide wire.

5. A system according to claim 1 wherein a guide ware is positioned in said central lumen of said second catheter.

6. A system according to claim 1 wherein the means for supplying agitation energy is a source of ultrasonic energy coupled with a piezoelectric band.

7. A system according to claim 1 wherein the means for monitoring pressures within an occluded zone of a vessel is a pressure transducer.

8. A system according to claim 1 wherein said central lumen includes therein a lumen occlusion means.

9. A system according to claim 8 wherein said central lumen occlusion means comprises a seal located on said guidewire.

10. A two catheter thrombolysis catheter system for the occlusion and treatment of a vessel obstruction comprising:

a. A first catheter having a catheter wall, a proximal end, a distal end, and first means for occluding a vessel located adjacent said first catheter distal end;

b. a second catheter having a catheter wall, a proximal end, a distal end, a central lumen which passes entirely through said second catheter and a second means for occluding a vessel located adjacent said second catheter distal end, said second catheter being slidingly engaged and coaxial with said first catheter so that the distance between said first means for occluding a vessel and said second means for occluding a vessel is variable and defines a treatment zone, said catheters being closely slidingly engaged so as to preclude the presence of an interluminal space between said catheters;

c. means in said second catheter for administering a thrombolytic agent into said treatment zone, said administering means including said central lumen of said second catheter and a plurality of radially disposed ports located in said second catheter wall between said first and second means for occluding a vessel, the ports being in fluid communication with said central lumen;

d. means in said central lumen of said second catheter for restricting the flow of thrombolytic agent therethrough;

e. means in said first catheter for aspirating said vessel, said aspirating means also being located between said first and second means for occluding a vessel; and f. means attached to said second catheter wall between said first and second means for occluding a vessel for supplying agitation energy in said vessel to said treatment zone.

11. A system according to claim 10 which further includes means associated with said second catheter wall for monitoring pressure within said treatment zone.

12. A system according to claim 10 wherein the means for supplying agitation energy is a source of ultrasonic energy coupled with a piezoelectric band.

* * * * *